United States Patent
Ju et al.

[19]

[11] Patent Number: 5,935,302
[45] Date of Patent: Aug. 10, 1999

[54] ION CHROMATOGRAPHY SYSTEM FOR CONDUCTING AN ENVIRONMENTAL ANALYSIS IN SEMICONDUCTOR EQUIPMENT

[75] Inventors: Jin-ho Ju, Seoul; Sang-kyung Kim, Yongin; Sung-chul Kang, Sungnam, all of Rep. of Korea

[73] Assignee: Samsung Electronics Co., Ltd., Suwon, Rep. of Korea

[21] Appl. No.: 08/991,246

[22] Filed: Dec. 16, 1997

[30]    Foreign Application Priority Data

Dec. 24, 1996  [KR]   Rep. of Korea ...................... 96-70903

[51] Int. Cl.[6] ............................ B01D 15/08; B01D 53/04
[52] U.S. Cl. ........................ 96/4; 96/10; 96/101; 96/354; 55/356
[58] Field of Search ....................... 55/356, 357; 96/4–6, 96/10, 351–354, 101, 105, 106; 210/656, 198.2

[56]    References Cited

U.S. PATENT DOCUMENTS

| | | | |
|---|---|---|---|
| 251,407 | 12/1881 | Bruns | 96/352 X |
| 3,486,307 | 12/1969 | McDermott | 96/353 X |
| 3,923,461 | 12/1975 | Barden | 96/4 X |
| 3,926,561 | 12/1975 | Lucero | 96/4 X |
| 4,201,550 | 5/1980 | Noszticzius et al. | 96/4 X |
| 4,468,948 | 9/1984 | Nakayama | 96/6 X |
| 4,834,877 | 5/1989 | Peters et al. | 96/6 X |
| 4,886,528 | 12/1989 | Aaltonen et al. | 96/6 |
| 4,900,448 | 2/1990 | Bonne et al. | 96/5 X |
| 5,078,759 | 1/1992 | Kira | 96/352 X |
| 5,100,555 | 3/1992 | Matson | 96/5 X |
| 5,133,862 | 7/1992 | Cannan et al. | 96/4 X |
| 5,482,859 | 1/1996 | Biller et al. | 96/5 X |
| 5,580,452 | 12/1996 | Lin | 96/5 X |
| 5,725,634 | 3/1998 | Takasuga et al. | 96/4 X |
| 5,759,237 | 6/1998 | Li et al. | 96/4 X |
| 5,785,741 | 7/1998 | Li et al. | 96/4 X |

*Primary Examiner*—Robert Spitzer
*Attorney, Agent, or Firm*—Jones Volentine, L.L.P.

[57]    ABSTRACT

An ion chromatography system analyzes the environment in semiconductor equipment for foreign materials. The system includes an impinger section for preparing a sample of the atmosphere, and an ion chromatography section. The impinger section includes an absorbent solution vessel, suction and exhaust piping connecting the vessel to the environment, and a pump for transporting atmosphere under pressure. The ion chromatography section includes a guard column, a separation column, and a detector. The suction pipe has an intake port positioned at a target site whose environment is to be analyzed. The impinger section is connected to the ion chromatography section so that the absorbent solution of the vessel directly enters the ion chromatography section. To promote the absorption of the atmosphere into the solution, the absorbent solution vessel may be in the form of an elongate diffusion scrubber having an outer cylindrical vessel and an inner tube made of a selective membrane. Alternatively, the vessel may incorporate a porous plate connected at the end of the suction pipe to break the sample of atmosphere into a plurality of gas bubbles.

18 Claims, 5 Drawing Sheets

5,935,302

ION CHROMATOGRAPHY SYSTEM FOR CONDUCTING AN ENVIRONMENTAL ANALYSIS IN SEMICONDUCTOR EQUIPMENT

BACKGROUND OF THE INVENTION

1. Field of the Invention

The present invention relates to an ion chromatography system for conducting an environmental analysis in semiconductor equipment and, more particularly, to a pretreatment section of such an ion chromatography system which can prepare and treat a sample efficiently and adequately.

2. Description of the Related Art

Manufacturing a semiconductor device requires precise processing technologies and a clean environment. It is necessary, therefore, to install special equipment for providing a clean environment such as a clean room in a semiconductor manufacturing facility. An exhaust system must also be arranged for removing foreign materials and particles from the environment of the facility. Various methods are used to check the environment in the clean room with the aim of ensuring that the level of the foreign materials is normal.

In such a semiconductor manufacturing facility, one known method of controlling the foreign materials in the atmosphere is the ion chromatographic method. In this method, air collected at a target position is passed through an absorbent solution such as pure water contained in a vessel of an impinger device, and ions of gas components dissolved in the absorbent solution are assayed using ion chromatography to check whether foreign materials are present in the atmosphere.

FIG. 1 is a schematic diagram of a conventional ion chromatography system. The ion chromatography system can precisely detect microscopic components of a sample by using the electric conductivity of ions in a medium such as pure water. Referring to FIG. 1, a separation device (not shown) first divides a sample from the sample feed inlet 14 into anionic and cationic portions. For each side of the apparatus shown in FIG. 1, sample feed control valve 11, which is regulated by an operator, directs the ion-separated sample to a sample loop 12, or directly to a discharge line 13. In a similar way, a carrier solvent used in the ion chromatography system is directed to a sample loop 12, or to the discharge line 13, or directly to a guard column 16 by a carrier solvent control valve 15. A part of the sample having a stronger affinity to the substances in the guard column 16 passes to a separation column 17 to carry the sample to a detector 18 based on the difference in the moving velocities of the substances.

In another ion chromatography system, a concentration column is used instead of the sample loop for analyzing highly pure water so that a concentrated sample is carried to a guard column, or an original sample is directly transported to the guard column by using an injector.

Because the ion chromatography system is an analytical instrument which detects the electrical conductivities of ions in a liquid phase, its ability to analyze for microscopic components of the atmosphere is limited.

Two type of methods are used in the preparation of a sample of atmosphere: a simple method and an atmospheric pressure transporting method.

In the simple type method, an absorbent solution contained in a vessel having a wide opening is placed at a desired position for a designated time period in order for the atmosphere at that position to naturally dissolve in the absorbent solution.

FIG. 2 shows a conventional impinger device is used for carrying out the atmospheric pressure transporting type method of preparing a sample. An absorbent solution vessel having the shape of a barrel is partially filled with an absorbent solution 22. An inlet of the vessel 21 is closed with a seal 23 through which suction and exhaust pipes 24 and 25 pass. The suction pipe 24 is used to suction the atmosphere into the absorbent solution 22. The atmosphere, having passed through the absorbent solution 22 into the space above the solution, is discharged to the outdoors through the exhaust pipe 25. A pump 26 is installed in at least one of the two pipes so that the atmosphere outside the vessel can pass through the absorbent solution in order for soluble components of the atmosphere to be dissolved in the solution.

In both methods, a sample is prepared from the atmosphere collected at a desired position and carried into the analytical equipment. The conventional methods for analyzing the components of the atmosphere using the impinger device and ion chromatography system have some disadvantages.

First, the sampling point, where the atmosphere is collected and a sample is prepared, is not identical to the position where the analytical equipment actually carries out its analysis. External contaminants may be introduced in the sample while the sample is carried to the equipment and injected into it. The contaminants on the glass sample vessel may also be dissolved in the sample.

Secondly, proper measures cannot be taken immediately if an unexpected situation-occurs at the sampling point due to the time required for carrying the sample and injecting it into the equipment.

In addition, the conventional impinger device uses pipes for carrying the sampled atmosphere into the absorbent solution under pressure. This piping decreases the surface area of the atmosphere which is allowed to contact the solution, thereby lowering the absorption efficiency of the atmosphere components. Excessive time is thus required to dissolve soluble components in the absorbent solution.

SUMMARY OF THE INVENTION

Accordingly, an object of the present invention is to provide an ion chromatography system for conducting environmental analysis in semiconductor equipment, which substantially overcomes one or more of the problems, limitations and disadvantages of the related art.

More specifically, an object of the present invention is to provide an ion chromatography system which makes it possible to immediately analyze the atmospheric components at a desired position and to cope with any situation during the analysis.

Another object of the present invention is to provide an ion chromatography system in semiconductor equipment which prevents the possible contamination of a sample during a pretreatment step in which the sample is prepared by dissolving the target atmosphere in an absorbent solution.

To achieve these and other objects, the present invention provides an ion chromatography system for conducting an environmental analysis in semiconductor equipment, which comprises an impinger section for intaking a sample of atmosphere under pressure, and an ion chromatography section connected to the impinger section. The impinger section includes an absorbent solution vessel, suction and exhaust pipes connecting the vessel to the atmosphere, and a pump for drawing in a portion of the atmosphere. The ion chromatography section comprises a guard column, a separation column, and a detector. An intake port of the suction pipe is located at a target site where a sample of the atmosphere is to be analyzed. The impinger device is connected to the ion chromatography section so that the absorbent solution of the vessel directly enters the sample feed inlet of the ion chromatography section.

A data analyzer may be connected to the detector. This analyzer is mounted on a cart with the impinger section and the ion chromatography section. Thus, the system can be easily transported to a desired target site.

The suction pipe has a multi-way (e.g., four-way, five-way, six-way) solenoid valve whose ports are respectively connected to various locations within the area to be analyzed. The solenoid valve is controlled so that the atmosphere at a desired location within the target area can be analyzed immediately.

The bottom of the absorbent solution vessel of the impinger section and the sample feed inlet of the ion chromatography are connected by a pipe having a control valve therein.

The impinger section further comprises an absorbent solution feed line and a pump that supplies the vessel with the absorbent solution.

Another specific object of the present invention is to provide an ion chromatography system which not only has the advantages described above but which, in addition, promotes the absorption of the atmosphere into the absorbent solution.

To this end, the present invention provides an ion chromatography system for use in environmental analysis in semiconductor equipment, which comprises an impinger section for intaking a sample of the atmosphere under pressure, and an ion chromatography section connected to the impinger section. The impinger section comprises a cylindrical absorbent solution vessel, suction and exhaust pipes connecting the vessel to the exterior of the system, and a pump for transporting atmosphere under pressure through the vessel.

The ion chromatography section comprises a guard column, a separation column, and a detector. The absorbent solution vessel of the impinger section is designed to increase the contact area between the atmosphere and an absorbent solution, thereby promoting the absorption efficiency. Specifically, the absorbent solution vessel includes a tube made of a selective membrane such as GORE-TEX and installed within a cylindrical vessel. The suction pipe opens at one end of the cylindrical vessel so as to introduce atmosphere into the vessel. The exhaust pipe opens at the other end of the cylindrical vessel, discharging the atmosphere flowing through the vessel. An absorbent solution supplier is connected to one end of the tube. Furthermore, a sample feed inlet connected to the other end of the tube connects the impinger section to the ion chromatography section.

The suction pipe is provided with a multi-way solenoid valve whose ports communicate with target positions where the atmosphere is to be analyzed, and with purge piping, respectively.

The absorbent solution vessel is elongate in the vertical direction so as to enhance the atmosphere absorption efficiency, and the outlet of the suction pipe is located at the bottom of the vessel, thereby requiring an extended time for gas bubbles to rise through the absorbent solution.

In another embodiment, the suction pipe extends into absorbent solution contained in an absorbent solution vessel of the impinger section. The outlet of the suction pipe is made of a plate having a multitude of injection pores arrayed across a wide area. These pores break the atmosphere into a plurality of gas bubbles. These gas bubbles have a surface area in contact with the absorbent solution that is much greater than if the atmosphere were merely introduced into the solution through a simple opening constituted by the end of a pipe. Accordingly, the absorption efficiency is enhanced.

A multi-way valve is installed in the suction pipe. One port of the multiway valve is connected to a nitrogen gas line to purge the target atmosphere with nitrogen gas.

BRIEF DESCRIPTION OF THE ATTACHED DRAWINGS

Other objects, features and advantages of the present invention will be described with reference to the accompanying drawings, in which.

Figure 4:
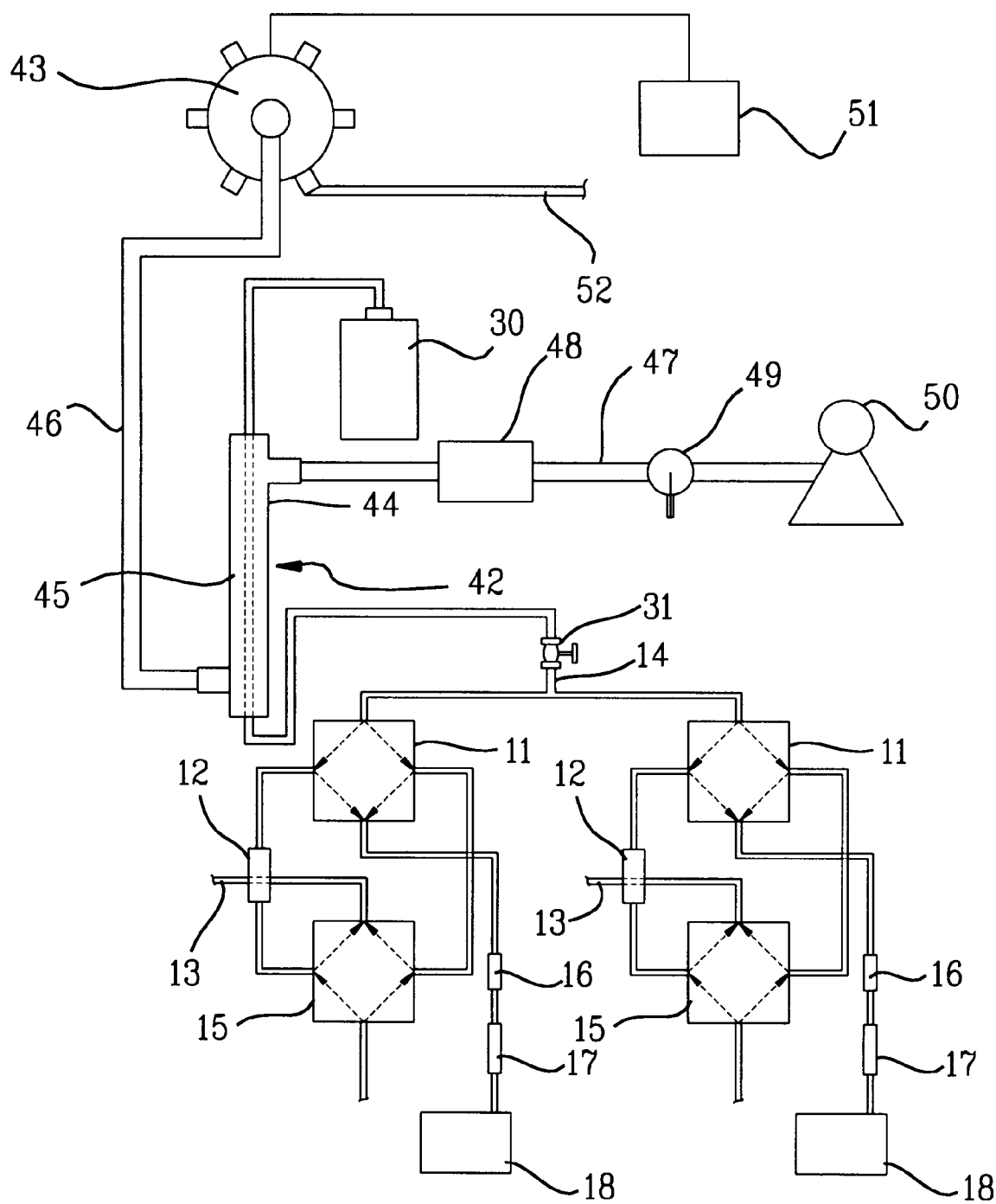
Figure 5:
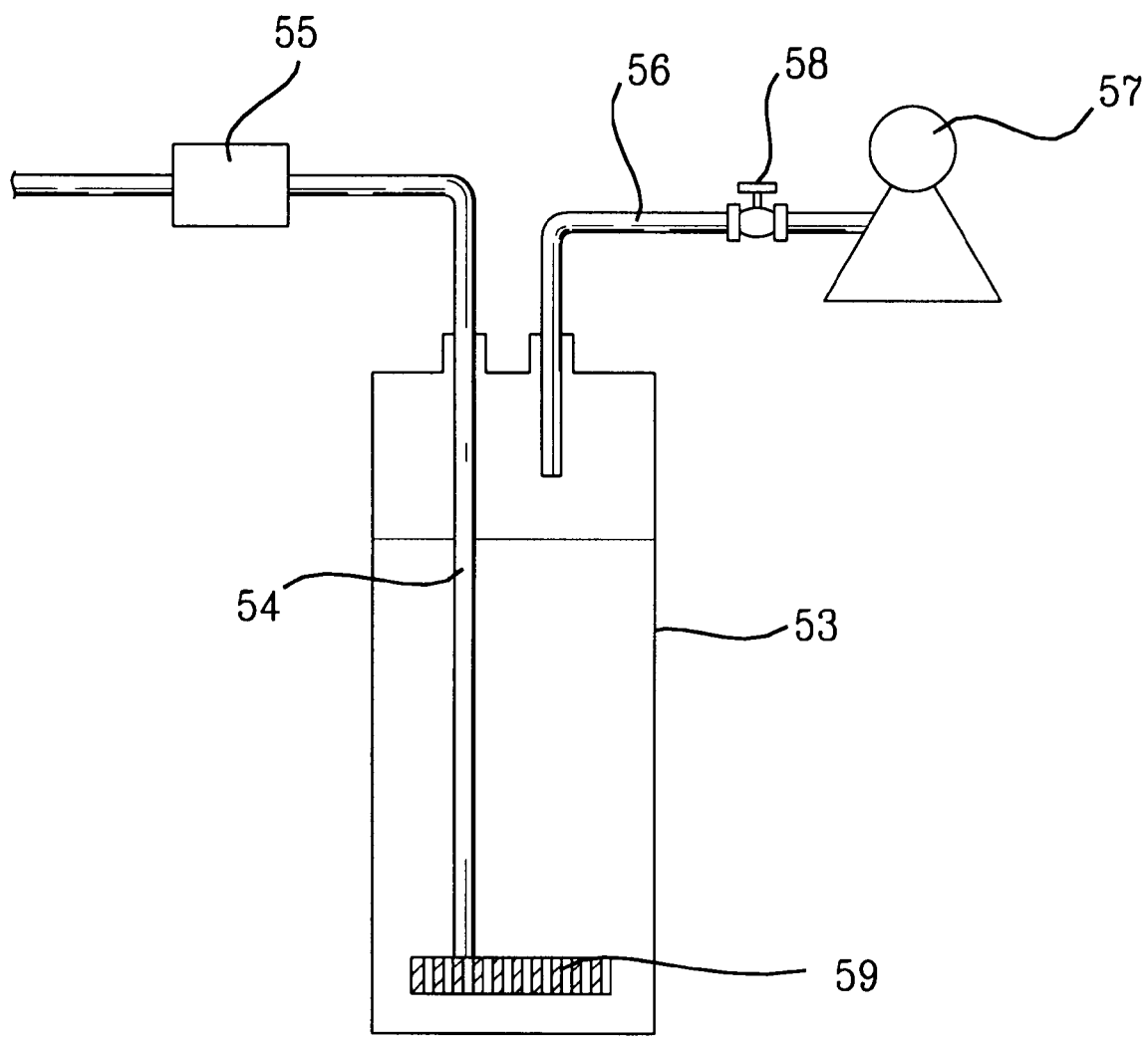

FIG. 4 is a schematic diagram of another preferred embodiment of an ion chromatography system for conducting environmental analysis in a semiconductor facility according to the present invention; and FIG. 5 is a schematic diagram of an impinger device of a preferred embodiment of an ion chromatography system that increases the contact area between a sample of atmosphere and absorbent solution according to the present invention.

DETAILED DESCRIPTION OF THE PREFERRED EMBODIMENTS

Reference will now be made in detail to the preferred embodiments of the present invention, examples of which are illustrated in the accompanying drawings.

Figure 1:
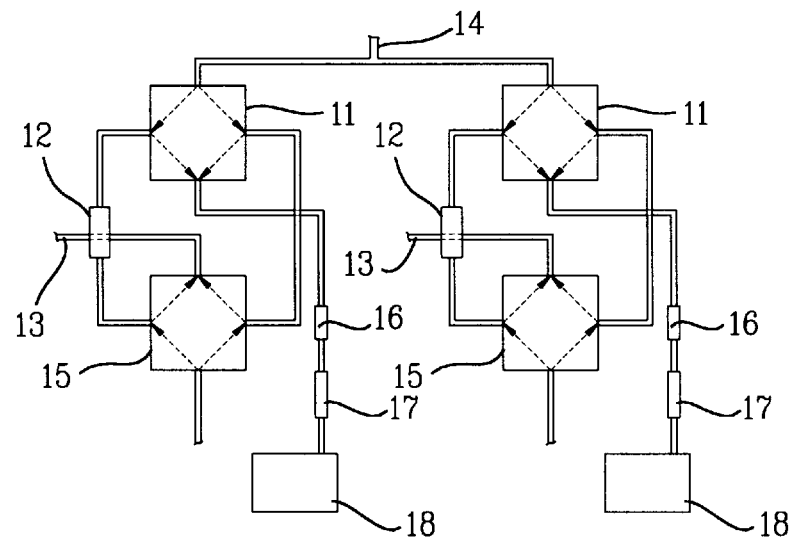
FIG. 1 is a schematic diagram of a conventional ion chromatography system.
Figure 2:
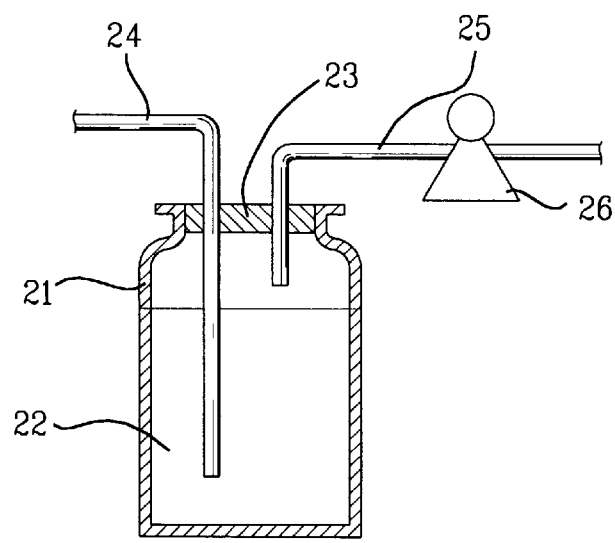
FIG. 2 shows a conventional impinger device.
Figure 3A:
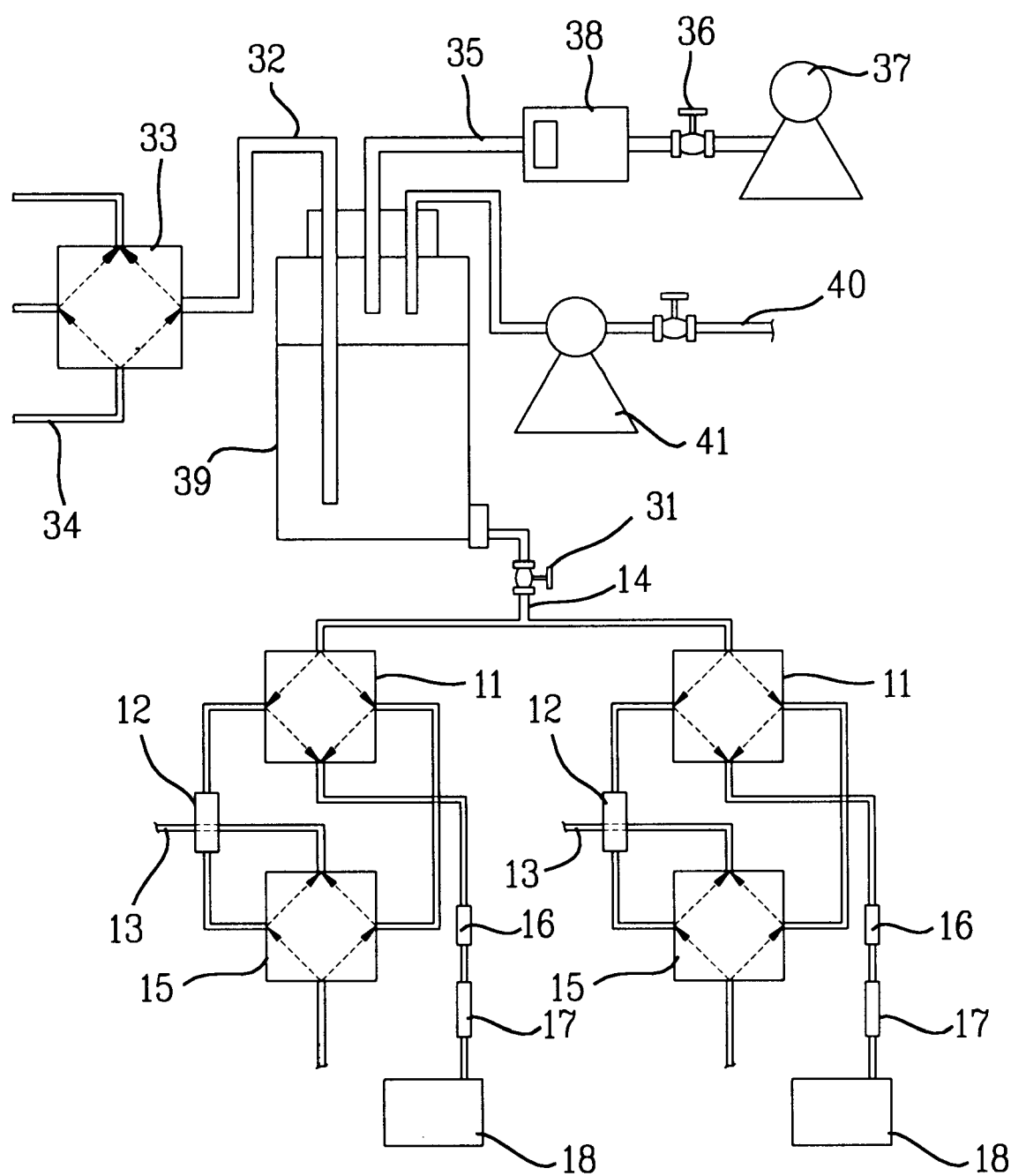
FIG. 3A is a schematic diagram of a preferred embodiment of an ion chromatography system for conducting environmental analysis in a semiconductor facility according to the present invention.

FIG. 3A is a schematic diagram of a preferred embodiment of an ion chromatography system for use in conducting environmental analysis in a semiconductor facility according to the present invention.

The system generally has two sections: an impinger section which is a pre-treatment section of the system located at the top of the system, and an ion chromatography section located at the bottom of the system. The ion chromatography section has a structure similar to that of a general sample loop system.

The impinger section has a sample feed inlet 14 for admitting an absorbent solution to the ion chromatography section once a connection valve 31 is opened. A suction pipe 32 is provided with a 4-way valve 33 connected to a nitrogen gas line 34 used for purging the section. An exhaust pipe 35 is connected to a valve 36, a vacuum pump 37 and a flow meter 38. The pipe 35 communicates with a pure water line 40 and a pump 41 that supply an absorbent solution vessel 39 with pure water serving as the absorbent solution. The vessel 39 is made from PTFE (Polytetrafluoroethylene) to suppress contamination due to any foreign materials emanating therefrom.

An analytical sample is fed to the ion chromatography section as follows. The pump 41 in the pure water line 40 is first operated, with the connection valve 31 closed, so that the absorbent solution is pumped into the vessel 39. Once the atmosphere is introduced into the 4-way valve 33 of the suction pipe 32, the vacuum pump 37 is operated in order to pass a given amount of atmosphere through the absorbent solution for a designated time period. When the operation of the vacuum pump 37 is stopped, the absorbent solution containing atmosphere components dissolved therein is fed to the sample feed inlet 14 by opening the connection valve 31.

The sample fed to the inlet 14 is then ready to undergo a qualitative analysis in the ion chromatography section. In the ion chromatography section, the anions and cations in the sample are separated and analyzed by an electrical conductivity detector 18. The absorbent solution remaining in the vessel 39 is discharged from the impinger section. Air remaining within the device is purged by regulating the 4-way valve 33 to admit nitrogen through gasline 34 and operating the vacuum pump 37.

Figure 3B:
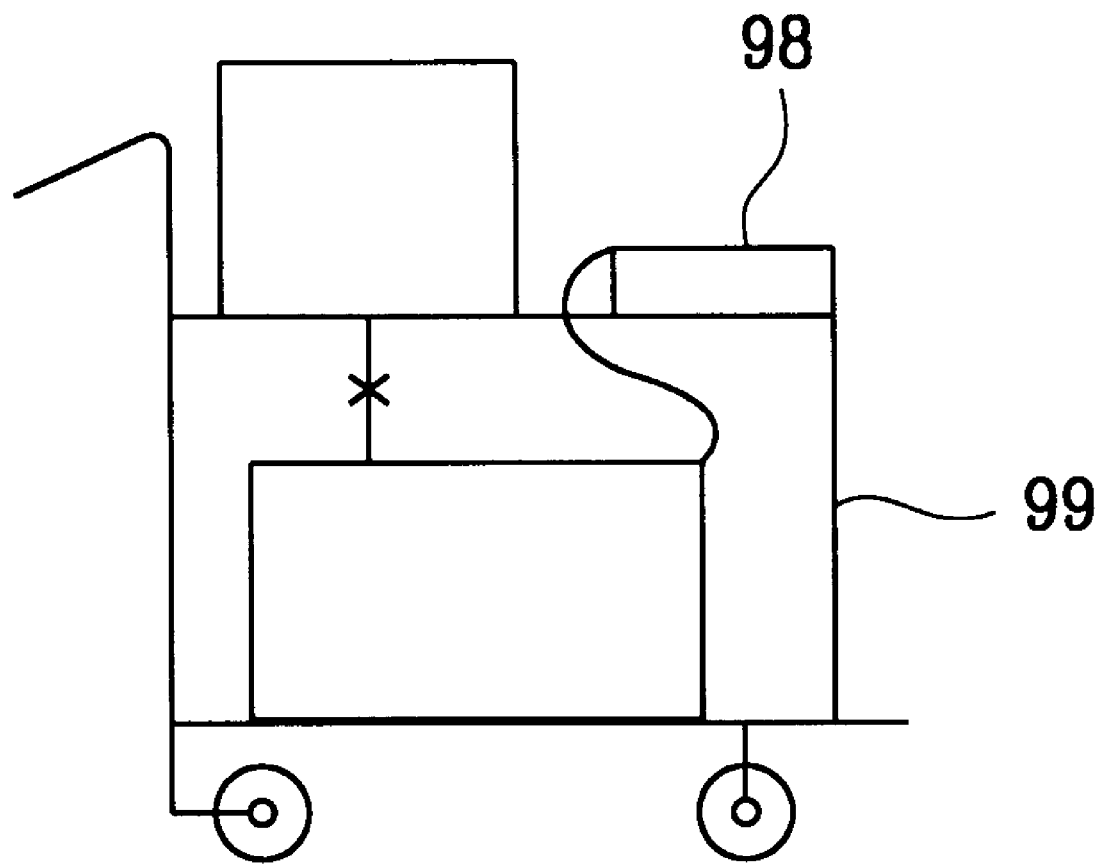
FIG. 3B is a schematic diagram of the system shown in FIG. 3A as designed to be readily transportable.

As shown in FIG. 3B, the ion chromatography system of the present invention employs a notebook computer 98 as a data processor and is installed on a cart 99. Consequently, once the system has completed an atmosphere analysis at one site it can be easily moved to another site for the purpose of carrying out a second analysis.

FIG. 4 is a schematic diagram of another preferred embodiment of an ion chromatography system for use in conducting environmental analysis in a semiconductor facility according to the present invention. As before, the lower ion chromatography section is of a sample loop type. The upper impinger section comprises an absorbent solution supply 30 (e.g., a container), an absorbent solution vessel in the form of a diffusion scrubber 42, and suction piping 46 connected to a multi-way (e.g., six way) solenoid valve 43.

The diffuision scrubber 42 comprises a tube 45 made from a layer of GORE-TEX (manufactured by The Dupont Company) installed in a cylindrical vessel 44 of PTFE. The suction pipe 46 is connected to one end of the cylindrical vessel 44, to thereby admit atmosphere into the vessel. The other end of the cylindrical vessel 44 is connected to an exhaust pipe 47 for allowing the atmosphere flowing along the tube 45 to discharge out of the system. The ends of the tube 45 are respectively connected to the absorbent solution supply container 30 and a sample feed inlet 14 of the ion chromatography section.

The exhaust pipe 47 is provided with a flow meter 48, a valve 49, and a vacuum pump 50. Respective positions of the solenoid valve 43 place the suction pipe 46 in communication with different sites to be sampled via pipes. A programmable timer 51 controls the position of the solenoid valve 43. One position of the solenoid valve 43 also connects the pipe 46 to a pure nitrogen gas line 52. Nitrogen purges the resident gas in the impinger section so that the resident atmosphere from the prior analyzed site does not become part of the newly analyzed atmosphere, to thereby avoid the occurrence of "a memory effect". In addition, the nitrogen prevents carbon dioxide from being dissolved in the absorbent solution before the atmosphere is collected in the early stage of the preparation of a sample.

Once the timer 51 opens one port of the solenoid valve 43 and drives the vacuum pump 50 of the exhaust pipe 47, the atmosphere at a target site is suctioned into the cylindrical PTFE vessel 44 which forms the outer piping of the diffusion scrubber 42 (absorbent solution vessel). The atmosphere flows along the outer piping, coming into contact with the tube 45 installed within the diffusion scrubber 42. Recall that the tube 45 is made from a material such as GORE-TEX which leads to a preferential transport of the atmosphere, i.e., of components other than those present in the absorbent solution such as pure or oxygenated water. The atmosphere components are absorbed by the absorbent solution, but the remaining atmosphere is exhausted through the exhaust pipe 47. The absorption rate can be increased by regulating the tube 45 material, thickness, number of openings and length. The inner pressure of the diffusion scrubber 42 also affects the absorption rate.

Once a given amount of atmosphere passes through the diffusion scrubber 42 (absorbent solution vessel), the absorbent solution containing the atmosphere components in the tube 45 is fed into the sample feed inlet 14 of the ion chromatography section and is analyzed with a detector 18.

Suction is preferably employed to force the absorbent solution through the diffusion scrubber 42 so as to prevent any change in the velocity of flow which may occur at an exhaust end due to the evaporation of the solution passing through the tube 45. The absorbent solution supply container 30 is desirably positioned above the diffusion scrubber 42 by about 1m so that air bubbles are not formed in the absorbent solution through minute pores extending across the tube layer.

According to the embodiment, the system may be used as a central control system that is installed at a certain site, such as a control room, and monitors the overall environment of the factory by connecting the solenoid valve 43 to different locations in the factory.

FIG. 5 is a schematic diagram of a portion of an impinger device of the ion chromatography system that also increases the area of contact between atmosphere and absorbent solution according to the present invention.

An absorbent solution vessel 53 comprises a long PTFE cylinder. A lower end of suction pipe 54 extends to the bottom of the vessel. The suction pipe 54 is equipped with a flow meter 55 to regulate the amount of atmosphere that is suctioned into the vessel 53. An exhaust pipe 56 has a vacuum pump 57 and a valve 58 installed upstream of the vacuum pump 57. A discharge plate 59 formed at one end of the suction pipe 54 has a multitude of minute pores extending therethrough.

The numerous minute pores arrayed across the discharge plate 59 generate air bubbles on the rather large surface of the plate, thereby improving the absorption of atmosphere into the absorbent solution.

The flow meter 55, the control valve 58, and vacuum pump 57 in the exhaust pipe suction the atmosphere through the vessel 53 without allowing any reverse flow, thereby contributing to a precise and reproducible sample analysis.

Furthermore, the invention allows for proper measures to be taken immediately if an unexpected situation develops at the target position.

The embodiment reduces the possibility of sample contamination during pretreatment (in which the sample is prepared by dissolving target atmosphere in the absorbent solution) and due to contaminations from the vessel.

It will be apparent to those skilled in the art that various modifications and variations can be made to and in the present invention without departing from the spirit or scope of the invention. Thus, all such modifications and variations that come within the scope of the appended claims are seen to be within the true spirit and scope of the present invention.

What is claimed is:

1. An ion chromatography system for use in conducting an environmental analysis, said system comprising:

an impinger section, and an ion chromatography section connected to the impinger section;

the impinger section comprising an absorbent solution vessel, suction piping having one end opening into said absorbent solution vessel and another end connecting the vessel to a site at the exterior of the vessel, exhaust piping having one end leading from the interior of the absorbent solution vessel and another end located outside of said vessel, and a pump operatively connected to one selected of a group consisting of said suction piping and said exhaust piping for forcing under pressure a sample from said site through said absorbent solution vessel; and the ion chromatography section comprising a guard column, a separation column, a detector, and a sample feed inlet connecting said absorbent solution vessel thereto such that solution contained in said vessel directly enters the ion chromatography section.

2. The ion chromatography system as claimed in claim 1, and further comprising a cart, and a data processor connected to said detector, wherein said data processor, said impinger section and said ion chromatography section being mounted on said cart so as to be easily transportable to a target site.

3. The ion chromatography system as claimed in claim 1, wherein said suction piping of said impinger section further comprises a multi-way solenoid valve having a plurality of ports respectively connected to different locations within a testing site.

4. The ion chromatography system as defined in claim 3, wherein said impinger section further comprises a programmable timer operatively connected to said solenoid valve to control the position of the solenoid valve and thereby select which of said locations of said testing site is in open communication with the impinger section.

5. The ion chromatography system as claimed in claim 1, wherein said ion chromatography section further comprises a control valve connecting the bottom of said absorbent solution vessel of the impinger section and said sample feed inlet of the ion chromatography section.

6. The ion chromatography system as claimed in claim 1, wherein said impinger section comprises a multi-way valve installed in said suction piping, and a nitrogen line connected to said multi-way valve such that when said multi-way valve is in one position, nitrogen passing through the nitrogen line can purge said system of residuals.

7. The ion chromatography system as claimed in claim 6, wherein said impinger section comprises a flow meter installed in one of said suction and said exhaust piping.

8. The ion chromatography system as claimed in claim 7, wherein said impinger section further comprises an absorbent solution feed line and a pump connected to said absorbent solution feed line so as to supply the vessel with absorbent solution.

9. An impinger device for use in an ion chromatography system, said device comprising:

an absorbent solution vessel having a vertically elongate cylindrical outer vessel and an inner tube disposed within said outer vessel;

suction piping having one end opening into said absorbent solution vessel at the bottom of said cylindrical outer vessel thereof and another end connecting the vessel to a site at the exterior of the vessel;

exhaust piping having one end leading from the interior of said absorbent solution vessel at the top of said cylindrical outer vessel thereof and another end located outside of said vessel;

an absorbent solution supply operatively connected to said tube so as to supply absorbent solution therethrough; and a pump operatively connected to one selected of a group consisting of said suction piping and said exhaust piping for forcing under pressure a sample from said site through said absorbent solution vessel.

10. The impinger device as claimed in claim 9, wherein said inner tube is composed of a membrane that allows selected components to pass therethrough, said absorbent solution supply being connected to one end of said tube.

11. The impinger device as claimed in claim 10, said another end of said suction piping further comprising a multi-way solenoid valve having a plurality of ports respectively connected to target locations to be analyzed and to piping used to purge the device.

12. The impinger device as claimed in claim 11, and further comprising a programmable timer operatively connected to said solenoid valve so as to change the position thereof during a selected time interval.

13. The impinger device as claimed in claim 11, wherein said purge piping is a gas line used for purging the impinger section of residual atmosphere.

14. The impinger device as claimed in claim 10, wherein said membrane selectively passes gaseous substances.

15. An impinger device for use with an ion chromatography system, said device comprising:

an absorbent solution vessel;

suction piping having one end opening into said absorbent solution vessel and another end connecting the vessel to a site at the exterior of the vessel;

exhaust piping having one end leading from the interior of the absorbent solution vessel and another end located outside of said vessel;

a sample feed outlet for providing solution to the ion chromatography system;

a pump operatively connected to one selected of a group consisting of said suction piping and said exhaust piping for forcing under pressure a sample from said site through said absorbent solution vessel; and a plate disposed within said absorbent solution vessel at said one end of the suction piping, said plate having an array of injection pores extending therethrough such that a sample of atmosphere suctioned into said absorbent solution vessel through said suction piping is broken up by said plate into a plurality of bubbles.

16. The impinger device as claimed in claim 15, and further comprising a multi-way valve installed in said suction piping, and a nitrogen gas line for purging the impinger device of atmosphere with nitrogen gas, said multi-way valve having a respective port connected to said nitrogen gas line.

17. The impinger device as claimed in claim 16, and further comprising a flow meter disposed in said suction piping, and a control valve and a vacuum pump disposed in said exhaust piping.

18. The impinger device as claimed in claim 17, and further comprising an absorbent solution feed line connected to said absorbent solution vessel.

* * * * *